United States Patent [19]

Göhde et al.

[11] Patent Number: 4,756,427
[45] Date of Patent: Jul. 12, 1988

[54] METHOD AND APPARATUS FOR SORTING PARTICLES

[75] Inventors: Hildegard Göhde, Nottuln; Johannes Schumann, Münster, both of Fed. Rep. of Germany

[73] Assignee: Partec AG, Bottmingen, Switzerland

[21] Appl. No.: 110,032

[22] Filed: Oct. 14, 1987

Related U.S. Application Data

[63] Continuation of Ser. No. 774,835, Sep. 11, 1985, abandoned.

[30] Foreign Application Priority Data

Sep. 11, 1984 [CH] Switzerland .................. 4326/84

[51] Int. Cl.$^4$ .............................................. B07C 5/04
[52] U.S. Cl. ..................................... 209/3.1; 209/552; 209/606; 209/906; 356/39; 406/168; 406/183
[58] Field of Search ................ 209/3.1, 552, 606, 643, 209/906, 932, 644; 356/39, 335; 324/71.4; 250/222.2; 406/168, 183, 181, 175, 197

[56] References Cited

U.S. PATENT DOCUMENTS

| | | | |
|---|---|---|---|
| 3,550,771 | 12/1970 | Spyropoulos | 209/644 |
| 3,560,754 | 2/1971 | Kamentsky | 209/906 |
| 3,827,555 | 8/1974 | Kamentsky et al. | 250/222.2 |
| 4,175,662 | 11/1979 | Zöld | 209/552 |

OTHER PUBLICATIONS

J. Duhnen et al, "A New Fluid Switching Flow Sortor", *Histochemistry*, 1983, vol. 77, pp. 117–121.

*Primary Examiner*—Robert B. Reeves
*Assistant Examiner*—Donald T. Hajec
*Attorney, Agent, or Firm*—Walter C. Farley

[57] ABSTRACT

A sorting method is disclosed in which particles suspended in a fluid are conducted in a closed duct and pass a measurement location in which particles to be selected trigger a signal by a sensing device. At a downstream fork, a pressure wave generated in response to the signal diverts the stream containing the particles from one branch to the other. An apparatus for carrying out this method is disclosed and includes a supply duct for the particle stream, a measurement duct, a measurement position in the measurement duct, a fork downstream of the measurement duct leading to a sorting branch duct and waste branch duct, and a pressure wave generator which is disposed in one of the ducts leading away from the fork.

14 Claims, 8 Drawing Sheets

METHOD AND APPARATUS FOR SORTING PARTICLES

CROSS REFERENCE TO RELATED APPLICATION

This is a continuation of application Ser. No. 774,835, filed Sept. 11, 1985 and now abandoned.

The present invention relates to a method of automatically sorting microscopic particles conveyed in a fluid stream and to an apparatus for accomplishing the sorting.

BACKGROUND OF THE INVENTION

There are microphotometric methods for the measurement or sensing of morphological and biochemical properties of macroscopic groups of particles, cells, blood cells, tumorous cells and the like. These methods are based on the principle that, in a photometric apparatus, light which proceeds from each individual particle which is suspended in fluid and which is drawn or pushed through a measurement position, called the flow metering chamber, is detected using light-sensitive detectors such a photomultipliers or photocells and is measured according to its intensity and/or temporal distribution. The results of such measurements on individual cells are histograms which display pulse height distributions. Methods of this kind permit the measurement of up to several thousand cells per second. The principle area of application is in cell biology and, in particular, research into cancerous cells as well as experimental or quantitative cytology.

In addition, methods have been proposed for measuring the cells in the first instance individually or measuring their biochemical or morphological properties and, directly thereafter, sorting these cells on the basis of preselected criteria. Such sorting devices operate, for example, in accordance with the following principle:

After recording of the particle property within the flow metering chamber or in a fine free stream as the stream leaves a pore aperture, the suspension stream is broken down with the aid of a piezoelectric transducer into homogeneous fine droplets the diameters of which are in the range from a few microns to a few tens of microns. On the assumption that at a particular time after the photometric measurement a particular cell to be selected is present as a droplet in the suspension stream immediately before the dissociation of this particle-carrying fluid component, the fluid current is electrically charged. This means that the droplet, which becomes dissociated immediately thereafter, is also charged. The chain of charged and uncharged droplets is now conducted past an electrostatically charged pair of electrodes. At this point, only the charged droplets are deflected in the desired manner and are caught in a vessel. Devices are known for immediately depositing these cells in culture vessels in order, for example, to cultivate lines of cells which are ascribed to a respective particular selected cell. Such methods are used, for example, in genetic engineering.

In contrast to this "open" sorting system, closed arrangements have also been proposed (Zöld or Wiecorek or Kamentsky). The arrangement described by Kamentsky makes use of a piezoelectric transducer for the temporally brief disturbance of a particle stream which, being surrounded by particle free solution, passes a measurement chamber. The disturbance of the particle stream, initiated as the result of the presence of a particle of interest is intended to lead to a situation in which the stream is mixed so that the pertinent particle passes into the enveloping current which is otherwise particle free, from which it is conducted into a separate trap.

The device described by Wiecorek et al makes use of a capillary duct system with, for example, a Y-shaped fork which is situated, in the direction of flow of the suspension, down stream of the measurement position. A microscopically small air valve is situated in each arm of the Y-shaped fork. Plungers which are secured at piezoelectric membranes and which incorporate small pistons open and close these valves in accordance with the sorting decision which is made on the basis of the individual measurement values for the cells. In the system which is operated with vacuum, the opening of a valve leads to the inflow of air into the pertinent arm of the duct system and, thus, to a reduction in the rate of flow. With the correct choice of the period of delay which elapses between the measurement of the cell characteristics and the opening of a valve, one can cause the cells which are of interest to flow into one branch and the cells which are not of interest to flow into the other branch of the capillary system. This sorting device can be operated with one or two oppositely acting valves.

A further sorting device, which was proposed by Zöld, likewise operated with a closed fork capillary system, in which the individual duct branches were occluded to a greater or lesser extent by electrical discharge between microelectrodes and the "gas formation" caused thereby in order to deflect the cells which are of interest into the respectively desired duct.

The droplet sorter first discussed above comprises an open system in which microscopically small droplets (the size of droplets in fog) containing the cells must be conducted in free fall past electrically charged electrode plates charged to about 10-20 KV. It is very difficult, in the first place, to determine the time which elapses between the measurement, the charging of the droplet which then becomes dissociated from the fluid current and the time at which the droplet reaches the "target" area. The timing is complicated by the fact that the droplet is subject to movement by air currents and by friction with air. This time must, to a large extent, be determined empirically and does not necessarily remain constant. The quality of the sorting process (purity of the sample) must be determined by the rather troublesome procedure of once again measuring the "sorted" cells.

This technique also subjects the cells to a drastic pressure change in a short path. As the droplets are formed, the stream is ejected under pressure through a very small opening and thus go from a pressurized state to an unpressurized state in a very short distance, somewhat less than 1 mm. The cells are rather delicate and cannot survive this sudden depressurization which results in degassing and cell deformation.

A decisive further disadvantage of this arrangement is that a considerable proportion of the microscopically small droplets do not move in the desired manner into the collecting vessel. By reason of complicated charging conditions of the droplets on the one hand and of the parts of the apparatus on the other hand, and also because of the very small size of the droplets and their susceptibility to movement by air currents, a considerable proportion of the droplets move in an uncontrolled manner into the region in the vicinity of the instrument.

This is of very great importance because the cells are stained, for example, with fluorescent dyes which are as a rule mutagenic and carcinogenic, or contain radioactive substances (e.g., 3H-thymidine). The aerosol which is formed with cells labeled in such a manner represents a real danger to the operating personnel who can become contaminated to a considerable extent by inhaling.

A further disadvantage of such open sorting systems is that they cannot be operated over a relatively long period of time under sterile conditions. However, it is important to be able to operate under sterile conditions because the sorted cells are frequently intended to be the starting material for new cell cultures.

The disadvantage of the closed arrangement proposed by Kamentsky is that, after each individual sorting process, which presupposes a respective disturbance of the central current, i.e., the mixing of the central stream with the enveloping current, a comparatively long period of time elapses until the central current containing the cell has once again become established and stabilized. In addition to this, the separation of cells which are of interest is, to a considerable extent, dependent upon chance: not all desired cells move far enough away from the central current stream, as a result of the piezoelectric disturbance, to be in a position to be eliminated with certainty from the periphery of the fluid current. The system, which has been known for almost twenty years, could not be implemented as a practical matter because it does not accomplish the sorting in such a way as to give usable results.

The arrangement proposed by Zöld is not suitable for sorting cells with the objective of subjecting these to further cultivation. Cells are relatively fragile; they loose their vitality as a result of the required explosions. Moreover, the system is very costly because of the substantial discharges which must take place at short time intervals and at high frequency. The gases which are formed must also be removed quickly; gases would interfere with the sorting process because of their elasticity and the inclination of the system to natural oscillations.

In the arrangement of Wiecorek et al, the quantities of air which are introduced prove to be disadvantageous for similar reasons. The arrangement is accordingly relatively slow or sluggish and susceptible to oscillations because of the elasticity of the air. The microscopically small valves are difficult to produce, susceptible to breakdown and costly in terms of maintenance when it is remembered that, in the open condition, the air inlet slits have a width of only several microns to a few tens of microns. The sorting process requires constant monitoring and correcting of the fine adjustment of the width of the air inlet opening. The required supply of air renders sterile operation of the arrangement difficult.

SUMMARY OF THE INVENTION

Accordingly, an object of the present invention is to provide a sorting method, and an apparatus for performing this method, which do not suffer from the disadvantages of known systems and, more particularly, in which particles are sorted in a closed system under sterile, reliable and protective conditions.

A further object is to provide such an apparatus which is extremely simple to produce, operate and maintain.

In one aspect, the invention comprises a method of sorting small particles including the steps of providing a closed duct having an inlet and a fork at which the duct separates into two branch ducts, conducting a stream of fluid into the duct inlet with a stream of particles suspended therein, such that the particle stream normally flows through a first one of the branch ducts, providing a measurement station along the closed duct upstream of the fork for sensing a predetermined property of particles in the stream and for producing a signal when the property is sensed, and creating a pressure disturbance downstream of the fork in response to sensing the predetermined property in a specific particle at the measurement station so that flow into the first branch duct is momentarily disturbed as the specific particle reaches the fork, thereby interrupting particle stream flow into the first branch duct and causing the specific particle to flow into the second branch duct.

In another aspect, the invention comprises an apparatus for sorting particles comprising a fluid duct having a measurement region with an inlet and a fork at which said duct separates into two branch ducts, and first sensing means along the measurement region for sensing a predetermined characteristic of particles flowing therein and producing a sensing signal in response to the sensed characteristic. A fluid is supplied to the inlet with a stream of particles suspended in the fluid so that the stream normally flows into a first one of the branch ducts. Means for generating a pressure wave is disposed along one of the branch ducts so that the pressure wave is created in response to the sensing signal for temporarily diverting a segment of the particle stream into the second of the branch ducts.

The term "fork" as used herein refers to a separation of the single inlet duct into two channels which are preferably separated by an angle of between about 10° and about 45°. However, the angle can be greater or smaller and can even be 0°, i.e., a duct which simply has a separating wall which separates the duct into a waste duct and sorting duct.

The particles to be sorted are preferably supplied to a measurement position in a central fluid current which is surrounded by a particle-free solution, such as water. At the measurement position, the particles are excited to fluorescence, for example, using a microscope-incident light arrangement through a microscope objective. Other measurements such as the measurement of scattered light or the measurement of the electrical resistance can also be accomplished. Each measurement signal is analyzed in accordance with its amplitude or temporal distribution (duration) using devices which are known per se, for example, with the aid of a multi-channel analyzer or a computer.

In accordance with the invention, when a particle is to be selected, a normalized signal which is associated with the pertinent measurement signal is conducted to a high voltage generator which conducts a high voltage signal to a piezoelectric crystal column or stepping motor after a period of time which is dependent upon the rate of flow of the fluid through the duct and the spacing between the measurement position and the duct fork. Such a column typically expands by 20 to 40 microns when a DC signal in the order of 1000 volts per micron is applied. The piezoelectric column has an extension in the form of a plunger. The plunger is located in a vacuum-tight bushing in the measurement chamber in the region of one of the two capillary ducts. When a high voltage is applied, the plunger moves by a few tens of microns in a direction transverse to the duct. Temporal progress of this movement corresponds to the wave form of the high voltage signal. Either of two effects can be utilized here:

(1) If the plunger projects into the duct, the cross section of the duct will be constricted as the plunger moves. Less fluid thus flows in the direction of the receiving vessel (downstream) connected to this duct. It is important that the dimensions of the two duct branches should be selected so that the particles normally flow into the waste duct when the piezoelectric column is in its unexcited state. This same result can be achieved by appropriate choice of the pressure conditions, utilizing vacuum, to influence the rate of flow.

When the column is in its unexcited state, a portion of only the particle-free current flows into the second duct. The constriction caused by the excitation of the piezoelectric column, however, leads to a situation in which a portion of the fluid stream containing particles is deflected into the sorting duct as a function of the duration of the applied high voltage signal. This can be repeated for each particle to be separated from the main stream at a rate of up to 1000 times per second.

(2) If the plunger is located beyond the wall of the duct (e.g., in a blind duct branching away from the waste duct), the excitation of the piezoelectric column causes a pressure wave which travels in both directions in the duct associated with the piezoelectric column. This pressure wave caused an immediate deflection of the central current containing the particles into the sorting duct because the fluid is incompressible. The result of this is a very precise deflection, which can extend over a period of time as short as desired, of the particle stream into the sorting duct. In this arrangement, the plunger is associated with the waste duct.

Of the two effects, the second is the dominant one. This occurs in circumstances in which the end of the plunger is located beyond the wall of the duct and also in circumstances in which the plunger extends into the duct.

The process may be repeated up to 1000 times per second, corresponding to a rate of sorting of 1000 cells per second.

It is also possible to control this process by installing, in place of the voltage-dependent longitudinal expansion of a piezoelectric column or other mechanical device such as a stepping motor, a device with which exactly the opposite movement is carried out. Starting from a high voltage level, it is possible to apply zero voltage pulses which lead to the contraction of the piezoelectric column. This causes a brief negative pressure surge in which the cells are drawn into the duct to which the piezoelectric column is coupled. Clearly, in this arrangement, the plunger must be associated with the sorting suct. However, for reasons associated with the protection of the cells and sterile operation, it is more expedient to operate with pressure waves which are generated by a piezoelectric column coupled to the waste duct.

The device of the present invention has the advantages that is comprises a closed system and may readily be sterilized. It does not cause any contamination of the environment nor any danger to the personnel. Since there are no gases in the system there is also no elasticity. It is therefore not susceptible to oscillation and exhibits a particularly high rate of sorting.

A noteworthy advantage has become evident in practice: the system sorts either correctly or not at all. Accordingly, erroneous sorting operations are not possible apart from statistical coincidences occurring when the cell density in the fluid stream is too great. The selection of the time delay between measurement and deflection (generation of the high voltage signal) is very simple since the deflected cells are individually seen through the microscope eyepiece during initial calibration in the form of a streak. When sorting takes place correctly, the "point of deflection"—situated at the same place in the region of the fork —of the sorted cells is clearly visible at the same place in all cases. In contrast to other systems, the ducts have a width of 100 to 500 microns and are accordingly particularly wide. As a result of this, they exhibit low susceptibility to interference by dirt particles. Calibration takes only a few minutes or less as compared with hours for the above-described open system.

In order to impart full understanding of the manner in which these and other objectives are attained in accordance with the invention, particularly advantageous embodiments thereof will be described with reference to the accompanying drawings, which form a part of the specification and wherein.

DESCRIPTION OF PREFERRED EMBODIMENTS

The embodiment to be described was specifically designed for the sorting of cells having different DNA contents by the measurement of biochemical properties of Ehrlich ascites tumor cells of the mouse by means of the determination of the DNA content. This measurement is based on the principle that, after staining with the fluorescent agent, the cells to be measured emit fluorescent light when they are excited with short wavelength light in the measuring apparatus.

Figure 1:
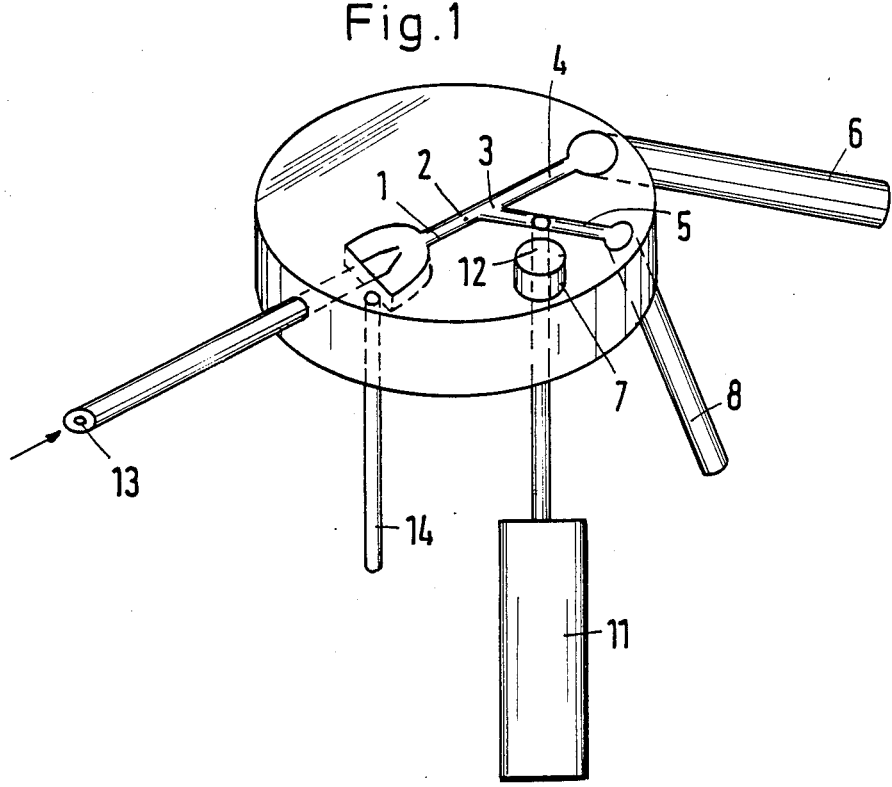
FIG. 1 is a somewhat schematic perspective view of a particle sorting device in accordance with the invention.
Figure 4:
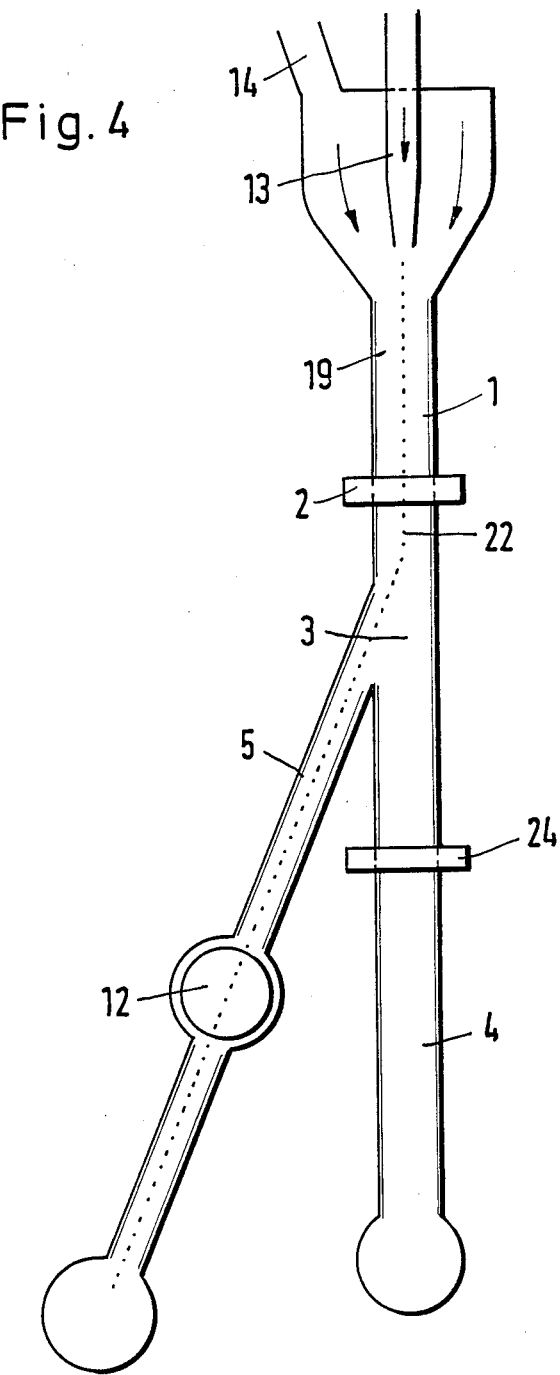
FIG. 4 is a schematic top plan view of a particle sorting device in accordance with the invention.

As will be seen in FIGS. 1 and 4, the fluorescent-labeled cells are conducted through a supply duct 13 which is a small, thin tube having an internal diameter of between about 100 and 300 microns, the stream of cells being delivered to a measuring duct 1. The measurement duct, which has a width of between about 1 and about 5 millimeters, passes through a second supply inlet 14 which delivers particle-free water 22 or some other solution acting as a dispersion medium for the cells. When the cell suspension arriving through small tube 13 and also the particle-free fluid delivered through tube 14 flow together into measurement duct 1, this results in the establishment of a laminar stream of cells which is essentially centrally located within duct 1 and which is surrounded by a tubular sheath of cell-free solution. This stream is very stable in measurement duct 1. The measurement duct has a cross section of, for example, 100 microns in height and about 200 microns in width and is therefore flat as viewed through a measurement objective lens 18. The measurement duct can be illuminated using a light source 17 and a half-silvered (semi-transparent) mirror 16.

The measurement duct leads to a fork 3 from which two branch ducts lead, one being a sorting duct 4 and the other being a waste duct 5. These ducts lead to outlet tubes 6 and 8. The stream of cells flows into the waste duct 5 when the stream is uninfluenced, i.e., duct 5 constitutes the normal path for the cells. The cells to be selected are conducted into the sorting duct 4.

Figure 2:
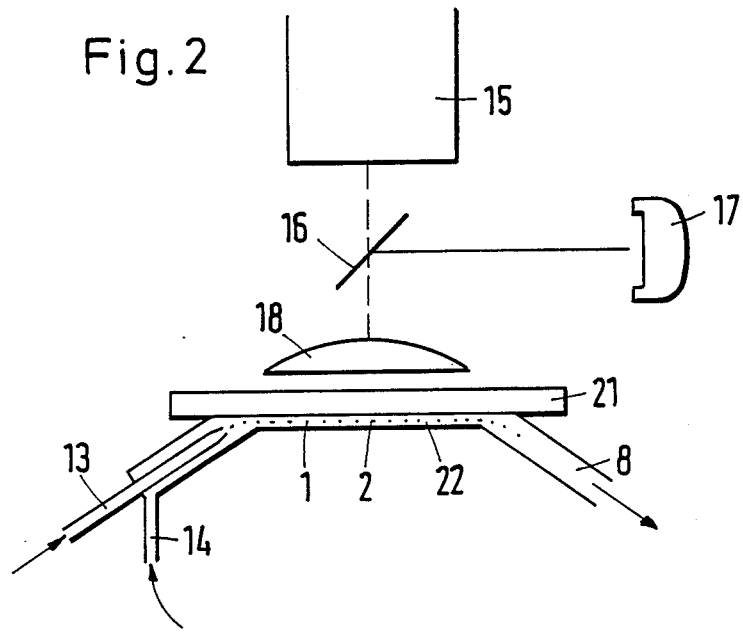
FIG. 2 is a side elevation in partial section through a particle sorting device employing incident light fluorescence.
Figure 3:
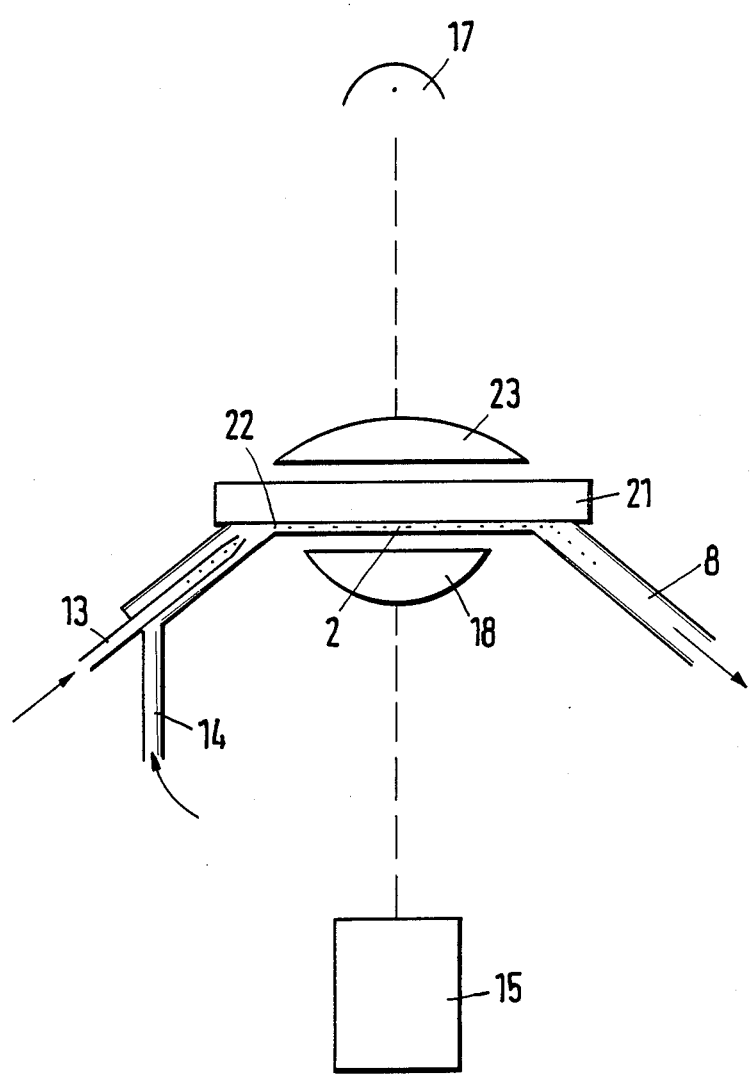
FIG. 3 is a side elevation in partial section through a particle sorting device using transmitted light for detecting fluorescence, absorption or scattered light.

Shortly upstream of the fork, as seen in the direction of flow, there is a measurement or sensing location 2 which can be observed through the measurement objective (FIGS. 2 and 3). In the region of this measurement location the cells which move individually through it are excited to fluorescence. The fluorescence passes through the measurement objective to a photomultiplier 15 for the measurement of the intensity of the measurement signals associated with each individual cell. These measurement signals are recorded and classified by electronic means which are, at present, conventional and not per se part of the present invention.

Instead of using only one objective for illumination of the measuring position and for the collection of the fluorescent light (incident light fluorescent measurement), it is also possible to use a separate objective 23 for the collection of the fluorescent light (transmitted light arrangement).

Figure 5:
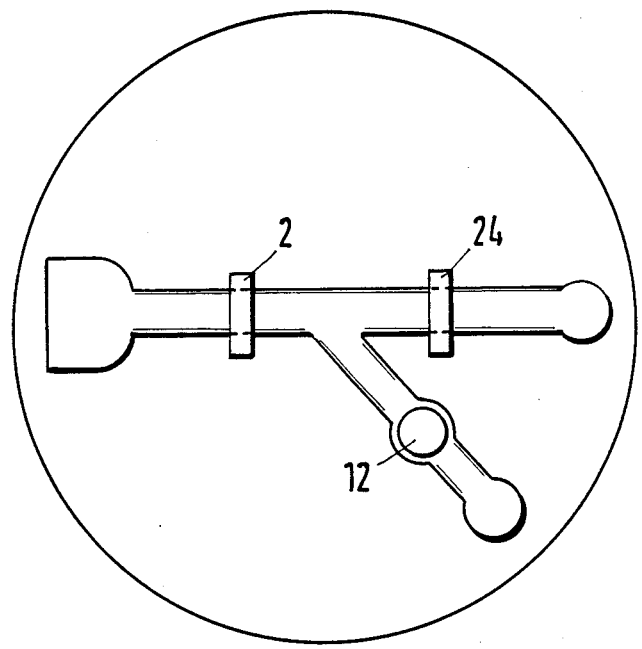
FIGS. 5 and 6 are schematic top plan views of portions of different embodiments of particle sorting devices in accordance with the invention.
Figure 7:
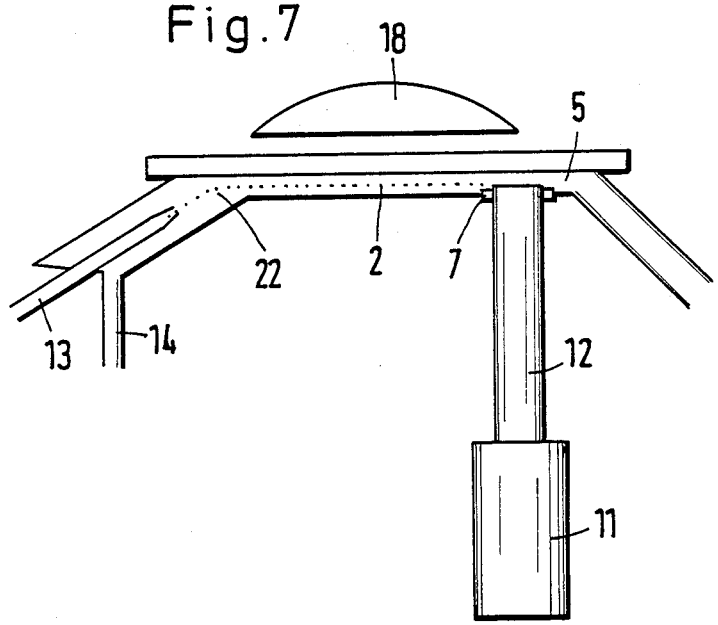
FIG. 7 is a side elevation in partial section of a further embodiment of a particle sorting device in accordance with the invention.

At the waste duct 5 there is disposed a pressure wave generator in the form of a piezoelectric column or stepping motor 11 which is provided with a plunger 12 which can be inserted into the duct (FIGS. 5 and 7). The opening through which plunger 12 projects into the duct is provided with a vacuum-tight bushing 7. Depending upon whether at any particular time the piezoelectric column is or is not excited by a signal, the plunger 12 projects to a greater or lesser extent into the duct 5. On the basis of predetermined algorithms or signal windows established by the electronic evaluation system, a preselection can be made as to what types of cells with specific properties are to be selected. In every case where such a cell is sensed by the measuring apparatus, the electronic system makes a decision to switch on the energy supplied to the piezoelectric column.

Figure 6:
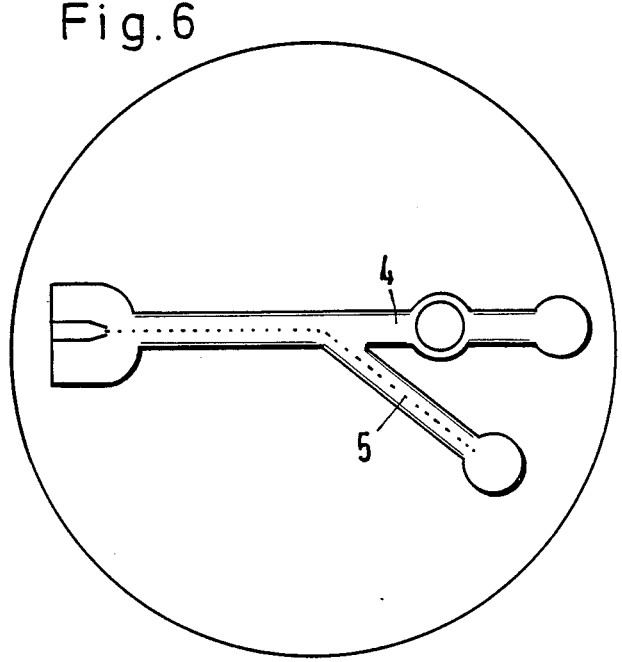

It is also possible, of course, to dispose the pressure wave generator at the sorting duct 4. This alternative is shown in FIG. 6. For this purpose, the plunger 12 of the piezoelectric column 11 must move in the opposite direction so that the system is operated with what can be called a negative pressure wave. It is particularly important that the fluid current should flow continuously into both ducts so that the laminar flow remains in existence and is not disturbed. In the event of complete occlusion of one duct, the laminar flow would be broken down and the central particle stream be mixed with the enveloping current.

Figure 8:
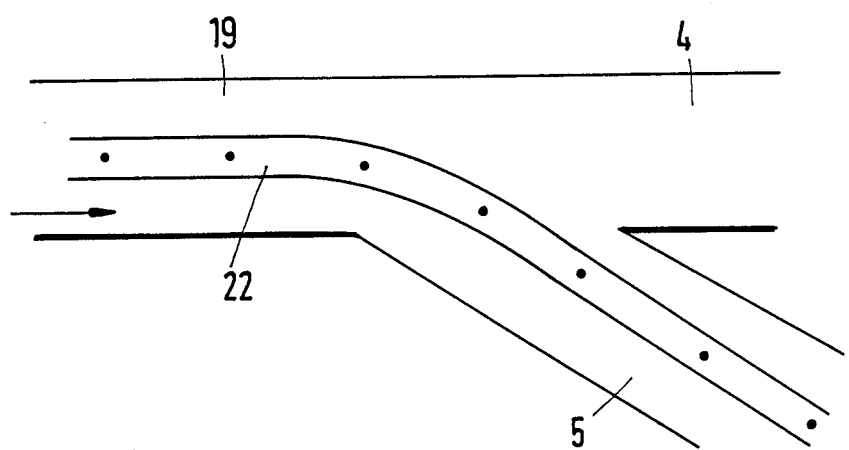
FIGS. 8 and 9 are schematic top plan views, at an enlarged scale, showing steps in the sorting of a particle.
Figure 9:
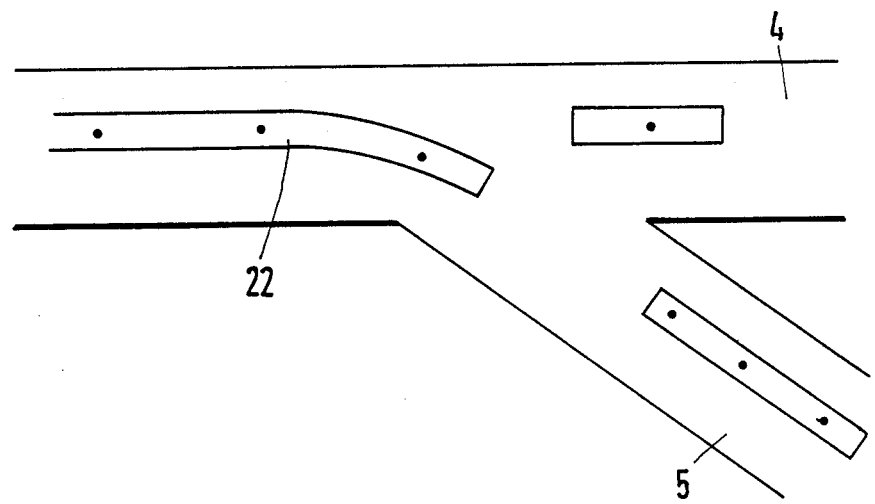

When a brief signal is applied so that the piezoelectric column is excited for a short interval of time and a short pressure wave is thus produced, the result of this is a brief temporary deflection of the laminar particle stream into the sorting duct 4 as illustrated in FIGS. 8 and 9. With the aid of suitable electronic means for time control, it is possible to ensure that the piezoelectric column is switched with the correct delay so that the excitation of the column in all cases takes place precisely at the time when the cells to be sorted are situated directly in front of the fork. In a specific embodiment of the apparatus, the rate of flow of the laminar current amounts to approximately 0.20 to 2.0 meters per second, depending in each case upon the pressure or vacuum applied for the transport of the currents.

The interval of delay between the sensing of the cell property and the switching of the piezoelectric column is varied as a function of the desired rate of flow. In this specific embodiment, the interval is between 20 and 200 microseconds. This time is also dependent upon the distance between the measurement position and the fork. FIG. 9 illustrates, in comparison with FIG. 8, how a short column of fluid in the particle stream is deflected from the waste duct current into the sorting duct by actuation of the piezoelectric column.

In the sorting duct 4, there can be disposed a further measurement position 24 which is illuminated and observed through the same objective (FIGS. 4 and 5). This means that each cell which passes this second measurement position gives a second sensing signal. Since only the selected signals are to flow in this duct, the measurement values of the selected cells are obtained in this manner without the selected sample having to be measured again in a second measurement process.

Figure 10:
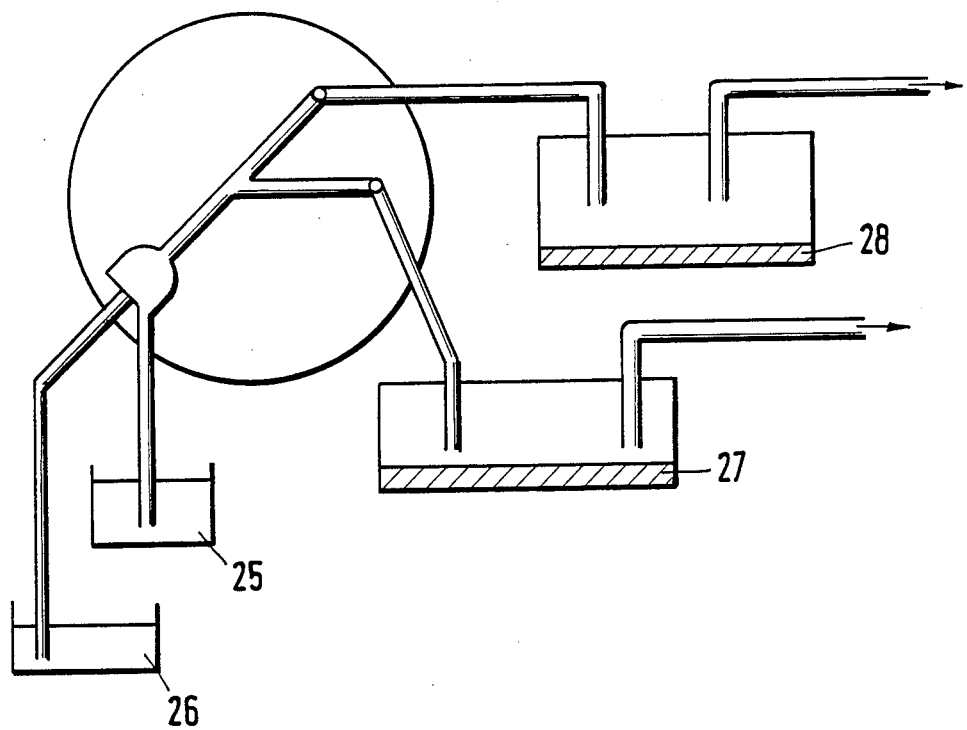
FIG. 10 is a schematic view of an overall system employing a particle sorting device in accordance with the invention.

FIG. 10 shows a schematic view of an overall system including a particle sorting device in accordance with the invention, the system including individual fluid containers which are shown in their arrangement relative to the sorting device. As shown therein, a container 25 supplies particle-free fluid through canal 14 to the particle sorting device to form the enveloping, surrounding current which encloses and centralizes the particle stream supplied through channel 13 from container 26. Waste particles, i.e., those which were not selected, are conducted to a chamber 27 which can be a closed chamber having a vacuum applied thereto in order to assist in the control of the flow rates of fluids through the device. Similarly, selected cells which are sorted and deflected into channel 4 are delivered to a chamber 28 which can also be evacuated, not necessarily to the same extent as chamber 27, for the purpose of controlling fluid flow. It would normally be the case that a stronger vacuum would be applied to chamber 27 than chamber 28 to thus induce normal flow to channel 5.

Figure 11:
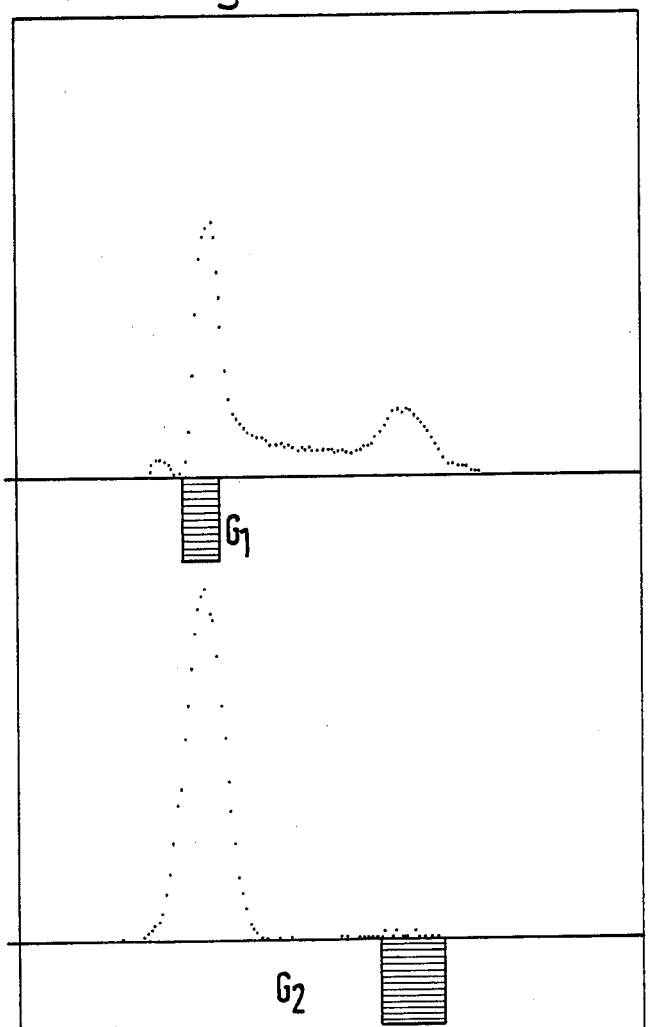
FIG. 11 is a histogram of DNA cells sorted on the basis of different DNA content.

FIG. 11 shows an example of the result of sorting of various size categories of DNA cells. In each case, the vertical or y axis is the numbers of cells while the x axis is calibrated in terms of size categories. Thus, the upper part of FIG. 11 shows the number of all cells in their distribution by size categories. When the measurement apparatus is set to select cells in a size category $G_1$, the cells belonging to this size category are sorted. When the measurement window is set to $G_2$, the number of cells associated with this measurement value is indicated.

The distribution of the cells selected with the window $G_1$ is shown in the middle portion of the graphical representation while the distribution of the $G_2$ cells is represented in the bottom of FIG. 11.

The areas of application of the method and apparatus in accordance with the invention specifically include the following:

(1) Sorting of different blood cells, leukemia cells;

(2) Sorting of different cells from tissue cultures;

(3) Sorting of different tumorous cells from human tumor biopsies in order to have these assessed by a pathologist. This is of importance because, in many cases, only very few tumorous cells are present in the samples and a preliminary enrichment thereof facilitates diagnosis. This is of particular importance within the context of early detection of cancer in mass surveys such as, for example, in vaginal cytology;

(4) The selection of particular cells provided with surfaced markers after labeling with antibodies, for example, for the purpose of cultivation of specific cell clones within the context of genetic engineering;

(5) Isolation of specific types of yeast infermentation for commercial purposes and biotechnology; and (6) The sorting of different microscopically small particles in industry such as colored pigments and other forms of particles in the pharmaceutical industry.

The method is particularly useful when all particles from which sorting is to be made are in the size range from 1 micron to a few hundreds of microns.

While certain advantageous embodiments have been chosen to illustrate the invention, it will be understood by those skilled in the art that various changes and modifications can be made therein without departing from the scope of the invention as defined in the appended claims.

What is claimed is:

1. A method of sorting small particles including the steps of
   providing a closed duct having an inlet and a fork at which the duct separates into two branch ducts;
   conducting a stream of liquid into the duct inlet with a stream of particles suspended therein, the particle stream normally flowing through a first one of the branch ducts;
   surrounding the stream of liquid with a particle-free enveloping current of liquid to produce substantially laminar flow;
   providing a measurement station along the closed duct upstream of the fork for sensing a predetermined property of particles in the stream and for producing a signal when the property is sensed; and
   momentarily altering the volume of a portion of one of said branch ducts to create a pressure disturbance downstream of the fork in response to the signal indicating sensing of the predetermined property in a specific particle at the measurement station without introduction of gas so that flow into the first branch duct is momentarily disturbed while the specific particle is at the fork while both branch ducts remain open to liquid flow, thereby interrupting particle stream flow into the first branch duct and causing the specific particle to flow into the second branch duct without eliminating the laminar flow.

2. A method according to claim 1 wherein the disturbance comprises a pressure wave generated in the first branch duct downstream of the fork, the wave causing particle stream flow to be momentarily diverted from the first branch duct to the second branch duct.

3. A method according to claim 1 wherein the disturbance comprises a pressure wave generated in the second branch duct downstream of the fork.

4. An apparatus for sorting particles comprising
   a fluid duct having a measurement region with an inlet and a fork at which said duct separates into two branch ducts;
   first sensing means along said measurement region for sensing a predetermined characteristic of particles flowing therein and for producing a sensing signal in response to the sensed characteristic;
   means for supplying a liquid to said inlet with a stream of particles suspended in said liquid so that said stream of particles normally flows into a first one of said branch ducts;
   means for supplying a sheathing liquid to said fluid duct to form a particle-free sheath surrounding said stream of particles; and
   means along one of said branch ducts downstream of said fork, for momentarily altering the volume of said one of said ducts in response to said sensing signal for generating a pressure wave and for temporarily diverting a segment of said particle stream into the second one of said branch ducts while both of said branch ducts remain open to liquid flow.

5. An apparatus according to claim 4 wherein said means for generating said pressure wave is located along said first one of said branch ducts.

6. An apparatus according to claim 5 and further comprising second sensing means located along said second one of said branch ducts for monitoring the particle sorting.

7. An apparatus according to claim 6 wherein said means for generating a pressure wave comprises a piezoelectric column coupled to said branch duct.

8. An apparatus according to claim 7 wherein said means for generating is located outside of said branch duct.

9. An apparatus according to claim 6 wherein said means for generating a pressure wave comprises a stepping motor attached to said branch duct.

10. An apparatus according to claim 9 wherein said means for generating is located outside of said branch duct.

11. An apparatus according to claim 5 wherein said means for generating a pressure wave comprises a piezoelectric column coupled to said branch duct.

12. An apparatus according to claim 5 wherein said means for generating a pressure wave comprises a stepping motor attached to said branch duct.

13. An apparatus according to claim 4 wherein said means for generating a pressure wave comprises a piezoelectric column coupled to said branch duct.

14. An apparatus according to claim 4 wherein said means for generating a pressure wave comprises a stepping motor attached to said branch duct.

* * * * *